(12) United States Patent
Meinecke et al.

(10) Patent No.: US 7,946,171 B2
(45) Date of Patent: May 24, 2011

(54) ANALYSIS DEVICE WITH HOUSING LOCK MECHANISM

(75) Inventors: Dieter Meinecke, Mannheim (DE); Stefan Riebel, Cham (CH); Wolfgang Pelzer, Kreuzau (DE); Wouter Reubzaet, Brunssum (NL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 284 days.

(21) Appl. No.: 12/047,877

(22) Filed: Mar. 13, 2008

(65) Prior Publication Data
US 2008/0257040 A1   Oct. 23, 2008

(30) Foreign Application Priority Data

Mar. 28, 2007 (EP) .................................. 07006359

(51) Int. Cl.
*G01D 11/24* (2006.01)
(52) U.S. Cl. ........................................................ 73/431
(58) Field of Classification Search .................. 206/807; 73/431
See application file for complete search history.

(56) References Cited

U.S. PATENT DOCUMENTS

| | | | |
|---|---|---|---|
| 1,487,885 A | 3/1924 | Raphael | |
| 1,716,246 A * | 6/1929 | Sparkes | 361/670 |
| 1,995,878 A | 3/1935 | Abbott et al. | |
| 2,081,627 A | 4/1936 | Heinrich | |
| 2,142,048 A | 12/1938 | Davis et al. | |
| 2,772,109 A | 11/1956 | Busch et al. | |
| 3,668,476 A | 6/1972 | Wrabel et al. | |
| 3,753,586 A | 8/1973 | Patterson | |
| 3,928,788 A * | 12/1975 | Finnen et al. | 361/664 |
| 4,068,288 A * | 1/1978 | Finnen | 361/664 |
| 4,416,478 A | 11/1983 | Canney | |
| 4,663,970 A | 5/1987 | Sutherland | |
| 4,834,706 A | 5/1989 | Beck et al. | |
| 4,875,486 A | 10/1989 | Rapoport et al. | |
| 5,904,588 A * | 5/1999 | Nimura et al. | 439/301 |
| 6,000,034 A | 12/1999 | Lightbody et al. | |
| 6,516,639 B1 * | 2/2003 | Margetts et al. | 70/57.1 |
| 6,685,085 B2 | 2/2004 | Hanna | |
| 2004/0138588 A1 | 7/2004 | Saikley et al. | |

(Continued)

FOREIGN PATENT DOCUMENTS

CA   2110315 A1   6/1994

(Continued)

*Primary Examiner* — Hezron Williams
*Assistant Examiner* — Nathaniel Kolb
(74) *Attorney, Agent, or Firm* — Justin L. Sage; Roche Diagnostics Operations, Inc.

(57) ABSTRACT

An analysis device is provided comprising a housing having at least two housing parts, a measuring unit and a processor provided therein for purposes of the functionality of the analysis device and generation of analysis data, wherein the device comprises a lock element for producing a generally fixed mechanical connection between the at least two housing parts. Providing such a lock element allows the analysis device to be checked for quality control and/or functionality purposes before the lock element is fitted to the housing, and if the device requires service or repair as a result of such checks then the housing can be reopened without damage to the housing or other aspects of the device. Once the lock element is fitted into a locked position for locking the housing together, subsequent reopening of the housing causes structural effects, including damage or destruction, to either or both of the lock element and the housing or housing parts, ensuring that such reopening becomes apparent to the user.

7 Claims, 2 Drawing Sheets

U.S. PATENT DOCUMENTS

2005/0227370 A1 10/2005 Ramel et al.
2006/0030194 A1 2/2006 Goetz

FOREIGN PATENT DOCUMENTS

| | | |
|---|---|---|
| DE | 4240327 | 6/1994 |
| FR | 970463 A1 | 6/1950 |
| GB | 850385 | 10/1960 |
| GB | 984593 | 2/1965 |
| GB | 1475543 | 6/1977 |
| GB | 2040267 A | 8/1980 |
| WO | 9819723 A1 | 5/1998 |
| WO | 2005054811 A2 | 6/2005 |
| WO | WO 2005/054846 * | 6/2005 |

* cited by examiner

ANALYSIS DEVICE WITH HOUSING LOCK MECHANISM

CLAIM OF PRIORITY

This application claims the priority benefit of European Patent Application No. 07006359.9, filed Mar. 28, 2007, which is hereby incorporated herein by reference in its entirety.

TECHNICAL FIELD OF THE INVENTION

The present invention relates generally to analysis devices for analyzing a medically significant component of a bodily fluid, and more particularly to such a device comprising a housing and a lock mechanism for locking said housing.

BACKGROUND

When using an analysis device for analyzing a medically significant component of a bodily fluid, such as blood or interstitial liquid, a qualitative or quantitative analysis is performed, i.e., for example, the presence, the absence, or the concentration of a specific analyte in a sample is determined. Exemplary known devices comprise a portable analysis device, operable by a patient for patient self-testing. Typical devices are configured for analysis or measurement of blood glucose, cholesterol, and blood coagulation parameters.

Analysis devices of this type comprise a device housing, a measuring unit situated in the device housing for performing the analysis on a sample, and a processor having software for processing the measured values ascertained by the measuring unit and for preparing the analysis measurement data from the measured values, typically taking into account calibration values. For example, the sample may be applied to a test element, such as a test strip, which is inserted through an opening in the housing of the analysis device and thereby into contact with the measuring unit. In other embodiments, analysis devices are also known in which sample (or more particularly a the test element wetted by a sample) is exposed to or contacted by a measuring sensor, which is located in the analysis device or projects therefrom. The use of magazines for test elements is also known in this context.

Test methods which work with test elements are typically used to a large extent for qualitative and/or quantitative analysis of components of a liquid sample, in particular a bodily fluid of humans or animals. The test elements typically contain reagents configured to react with the liquid sample or analytes therein. For example, to perform a reaction, the test element is brought into contact with the sample. The reaction of sample and reagents results in a change of the test element characteristic for the analyte, which characteristic is analyzed with the aid of the analysis device. The analysis device is typically capable of analyzing a very specific type of test element of a specific manufacturer. That is, the test elements and the analysis device typically form components mutually tailored to one another and are referred to as a whole as an analysis system.

Numerous different test element types are known, which differ in the measurement principle and the reagents used and in their construction.

Colorimetric analysis systems are an example of the use of one type of measurement principle. In such a system, the reaction of the sample with the reagents contained in the test element results in a color change therein, which may be measured visually or using a photometric measuring unit. Alternatively, electrochemical analysis systems are an example of another popular type of measurement principle, in which the reaction of the sample with the reagents of the test element results in an electrically measurable change (of an electrical voltage, electrical charge or an electrical current), which is measured using corresponding measurement electronics. Analysis systems of this type include what are referred to as amperometric systems; that is, those in which the measurement principle comprises the measurement of current.

In the context of analysis devices for analysis or measurement of analytes in bodily fluids, regular monitoring of specific analytical values of the blood is frequently necessary. This is true in particular for diabetics, who are to check their blood sugar level frequently using blood sugar self-testing, to keep their blood sugar level continuously within specific setpoint limits as much as possible by adapting insulin injections to the greatly varying demand. Checking blood coagulation parameters through a patient blood coagulation self test is also correspondingly common.

A blood glucose measuring device is a measuring device, with the aid of which the blood sugar content may be determined qualitatively or quantitatively. For this purpose, a piercing wound is typically generated in a body, a blood droplet is taken, the blood droplet is applied to the test element, and the blood glucose content in the drop is determined with the aid of the test element and the blood glucose measuring device. However, measuring the blood glucose by a permanent measurement, for example, using sensors inserted into the body or through the skin, is also conceivable.

Above all in the field of so-called "home monitoring", i.e., in which medical laypersons perform simple analyses of the blood themselves, and particularly therein for the regular blood acquisition to be performed multiple times daily by diabetics for checking the blood glucose concentration, it is important that simple and reliable operation of the blood glucose measuring device is possible and informative and reliable determination and display of the measurement results are provided.

The typical analysis devices are so-called standalone, portable measuring devices. These devices operate autonomously, self-contained, and independently. They thus typically comprise a display screen, a measuring unit, a power supply, and a user interface, which may comprise a keypad, a display, a signal generator, or a user guide, for example. The intended purpose and the properties of devices of this type are typically fixed, except for occasional adaptations of the firmware.

The present invention generally relates to the design and manufacture of analysis devices, and more particularly to the assembly of housing parts, as may be used for, e.g., blood sugar measuring devices. Typically, a housing for such a device comprises two parts, a housing upper shell and a housing lower shell. The housing also typically comprises operating elements within the surface of the housing, e.g., a keypad, pertaining to the particular device. During typical manufacture of a device, a functional check of the measuring device housed within the housing is performed after the two housing halves have been joined. This typically occurs as a last or near-final step in the assembly of the analysis device. Snap connections are frequently used according to the prior art to make the assembly of the housing halves as favorable as possible. Further disassembly of the housing halves which have been joined together in this way is usually not possible, because the assembly must meet the requirement of ensuring that the housing cannot be opened by the end-user (in order to protect the measurement device itself). Therefore, if flaws are discovered during the final functionality check, e.g., in the operating elements, then in order to repair the device, the housing must be opened, thereby destroying the housing halves.

In the past, analysis measuring devices have either been connected to one another by a screw connection or the housing parts are snapped together (as described above) in the final assembly step. Because it is important to ensure that it be recognizable whether a device has been previously opened, the typical snap connection is designed so that the mating components are destroyed upon reopening of the device. Also, if the housing is assembled using a screw connection, screws are normally covered by a seal, a label, or protective lacquer, which are designed so that the seal or label must be pulled off (which results in damage to the seal/label) or the protective lacquer on the screw must be obviously damaged when the device is opened.

After the assembly of a prior art analysis device, for example, from manufacture or after performing repair or maintenance, a final functionality test is typically performed. In order to do this, the device must be completely assembled. If a flaw becomes apparent at this point, the device must be disassembled again and repaired. The disadvantage of the screw connection and/or the nonremovable snap connection here is that after the disassembly, components may not be used again and increased costs thus occur. With a snap connection, the components having the snaps and/or snap receptacles are affected above all in this case. With parts which are screwed together, the reuse of the components having the screw bosses is critical. In addition, the use of screw connections increases the assembly effort and thus the costs.

Seals of containers or devices which prevent opening or allow only a single use of the device are known, for example, from the following publications: U.S. Pat. No. 3,753,586, U.S. Pat. No. 4,834,706, U.S. Pat. No. 4,875,486, U.S. Pat. No. 1,487,885, DE 4240327 C2, GB 984,593, GB 850,385, GB 2 040 267 A, U.S. Pat. No. 6,685,085 B2, WO 98/19723, US 2005/0227370 A1, U.S. Pat. No. 4,663,970, DE 27 53 285 A1, U.S. Pat. No. 2,772,109, U.S. Pat. No. 4,416,478, U.S. Pat. No. 2,142,048, FR 970,463, U.S. Pat. No. 2,081,627, U.S. Pat. No. 1,995,878, GB 1 475 543, all of which are hereby incorporated herein by reference in their entireties.

SUMMARY OF THE PRESENT INVENTION

It is an object of the present invention to provide an analysis device, the housing of which may be locked together during its assembly only after a functionality check is performed. In this way, it is secured against unwanted opening and/or such opening is recognizable on the device. In one embodiment, the lock element and/or the lock function is generally unnoticeable by the user of the device. In other embodiments, the present invention comprises a method for manufacturing an analysis device having an improved functionality check in the manufacturing process.

This object and others that will be appreciated by those skilled in the art in view of this disclosure are achieved according to the present invention by an analysis device and a method having the features of the attached independent claims.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses. Detailed description of embodiments of an analysis device from measuring blood glucose in a sample of blood or serum is thus intended to be exemplary in nature and shall not limit the scope of the invention to such embodiments.

Figure 1:
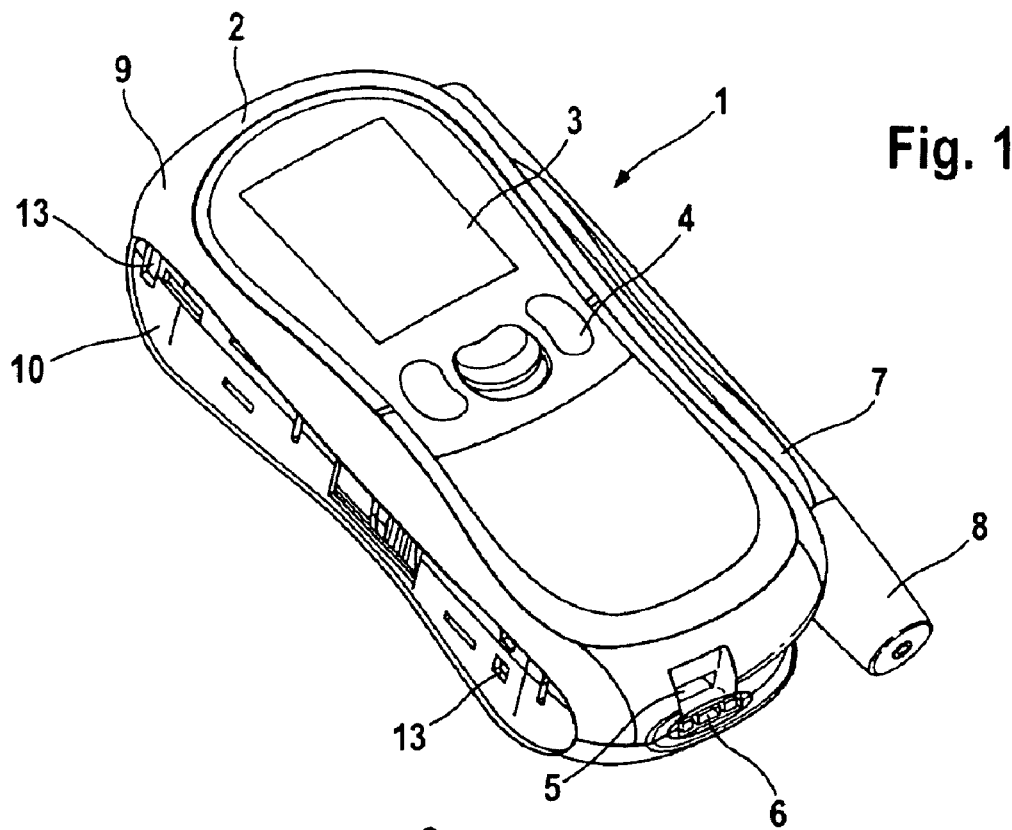
FIG. 1 illustrates an analysis device according to one embodiment of the present invention, in which the housing is assembled, absent a lock element according to the present invention.

FIG. 1 shows an analysis device according to the present invention. Such an analysis device 1 is, for example, an analysis device for analyzing a bodily fluid. In one embodiment, device 1 is configured for patient self-testing, for example, a blood glucose meter, a cholesterol measuring device, or a blood coagulation parameter measuring device. The embodiment of analysis device 1 shown in FIG. 1 is a generally portable analysis device, which may be manually handled, manually actuated, and manually operated by a patient, and is shown in the form of a blood glucose measuring device for patient self-testing of blood glucose values. This embodiment comprises a housing 2 having a display 3, operating elements 4, and an opening 5 for receiving at least a portion of a test element having a sample applied thereto (either before or after such receiving), the sample being analyzed using the analysis device 1.

A measuring unit for performing a blood glucose determination, for example, is provided within the housing 2 of the blood glucose measuring device. The blood glucose values are obtained from a blood droplet obtained from the patient, which is applied to a test field or region of a test element (not shown). The test element may be inserted through the opening 5 in the housing 2 of the blood glucose measuring device 1 and into the measuring unit located therein. Such a measuring unit may be a calorimetric or electrochemical measuring unit, for example. In other embodiments, the test elements are located in the housing 2, for example, in the form of magazines, and are wetted by the blood droplet through an opening in the housing 2.

The analysis device 1 may alternatively also be an integrated device having a strip magazine. This is to be understood to mean a device in which so-called integrated disposables are used. Integrated disposables are consumption elements which are characteristic in that they comprise both a needle element for performing the piercing procedure for obtaining a bodily fluid sample, such as a blood sample, and also a test chemical for performing the analysis of a medically significant component of the sample. Such disposables are frequently used in suitable magazines which have the form of a strip, for example.

A blood glucose measuring device in a typical embodiment performs the blood glucose determination using a processor, possibly taking into account calibration values, and transmits the ascertained analysis measurement data to the integrated display 3 and/or via an interface 6 to an external display or a computer.

In other embodiments, such as shown in FIG. 1, the analysis device 1 also comprises a holder 7 having a removable piercing apparatus 8 for obtaining the blood droplet for performing the analysis.

As shown in the illustrated embodiments, the housing 2 of the analysis device 1 comprises an upper housing part 9 and a lower housing part 10, which, like the remainder of the analysis device 1, with the exception of the lock element 11 still to be fitted onto the housing, are assembled into a generally mated orientation. After such assembly, the device is generally ready for performing a final functionality check (or any other quality control check, as desired). In one embodiment, the analysis device is generally functional for its basic purpose without a lock element 11 being fitted thereto (according to the description below). Thus, when the analysis device 1 is in a generally assembled form, with the exception of the lock element 11, functionality checks may be performed thereon and, if a repair is necessary, it may be opened generally without problems and without destroying parts.

Figure 2:
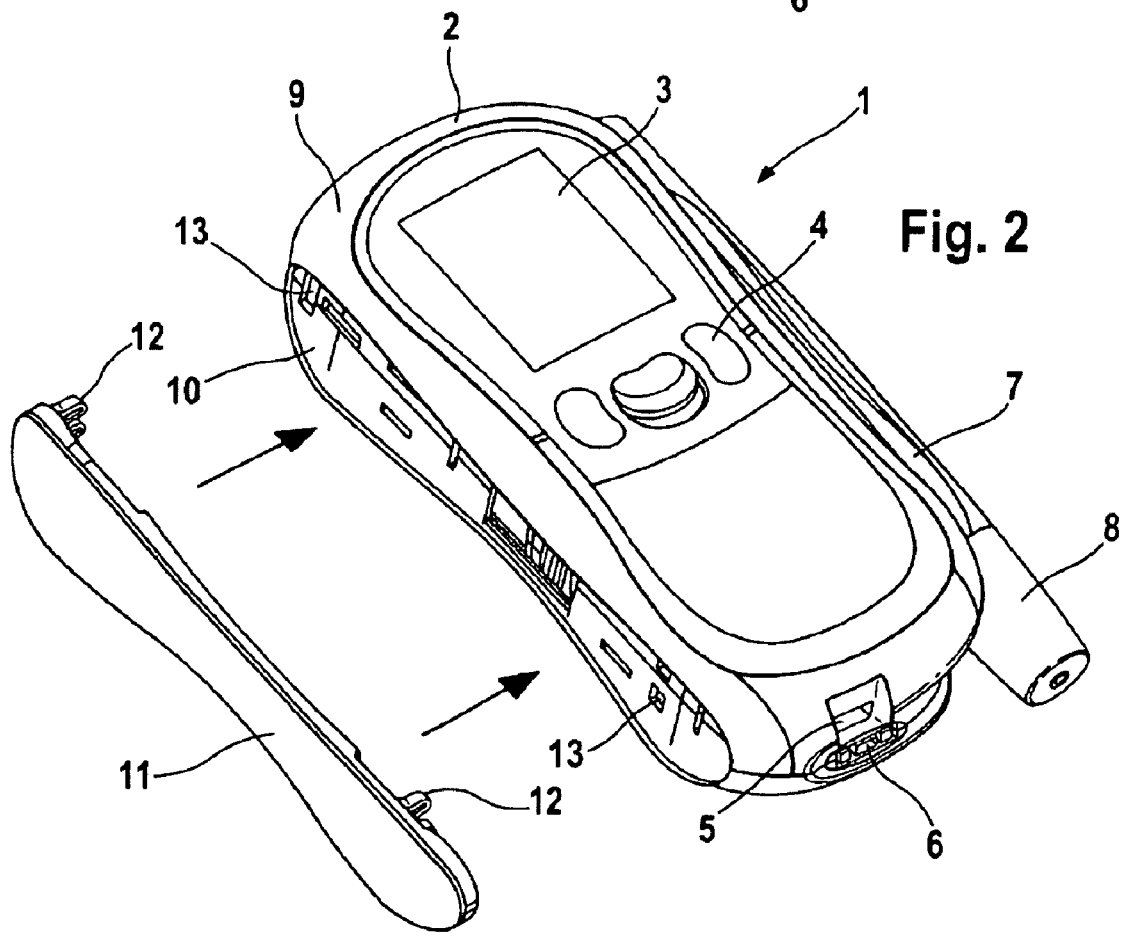
FIG. 2 illustrates the attachment of a lock element according to one embodiment of the present invention to the readily tested analysis device of FIG. 1.

Referring now to FIG. 2, a lock element 11 according to one embodiment of the present invention is fitted to the housing 1 of the analysis device 1 from FIG. 1, typically after all desired checks are completed, into a generally locked position. The lock element 11 may be fitted into the locked position such that the lock element 11 engages the housing parts 9, 10 in such a way that it is no longer possible to disassemble the lock element 11 without causing apparent structural effects on the housing 2 and/or the lock element 11, such as partial or complete destruction thereof. For this purpose, in the illustrated embodiments, the lock element 11 comprises catch hooks 12 which are configured for insertion into corresponding receptacle openings 13 of the housing.

Figure 3:
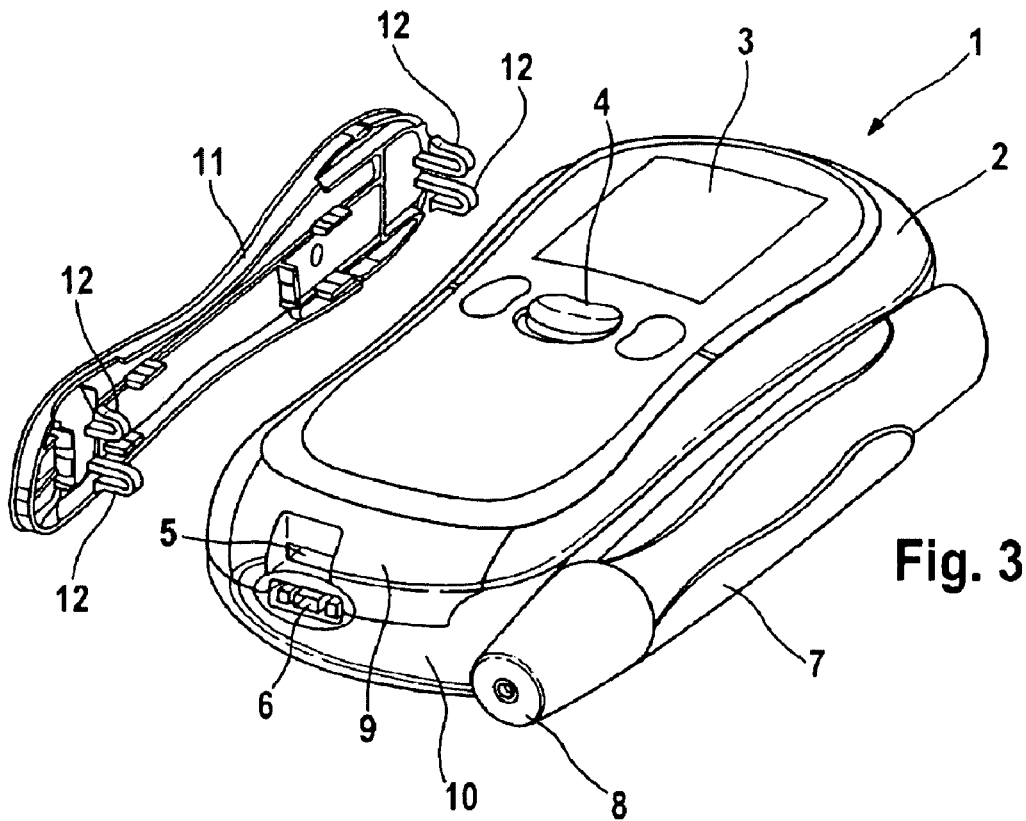
FIG. 3 illustrates another view of the embodiment of FIG. 2.

FIG. 3 shows another view of the embodiment of FIG. 2. It may be seen that in this exemplary embodiment, the lock element 11 has a total of four catch hooks 12, two on each end of the lock element 11, each pair having the catch hooks 12 being situated adjacent to one another, one for engaging in the upper housing part 9 and the other for engaging in the lower housing part 10. In other embodiments, catch hooks 12 comprise predetermined breaking points configured to break upon opening of the housing 2 and/or upon removal of the lock element 11 from the housing 2. Subsequent or unauthorized opening of the housing 2 is thus made apparent in this way.

In yet other embodiments, it is also possible that the lock element 11 does not have a predetermined breaking point, and is connected to the housing 2 in such a way, for example by catch hooks 12, that the lock element 11 is essentially destroyed upon opening of the housing 2 and/or upon removal of the lock element 11. In general, fitting the lock element 11 in a locked position for locking the housing 2 is configured so that reopening the housing is precluded without the reopening being apparent from structural effects on the housing 2 or the lock element 11 being caused by such reopening.

Figure 4:
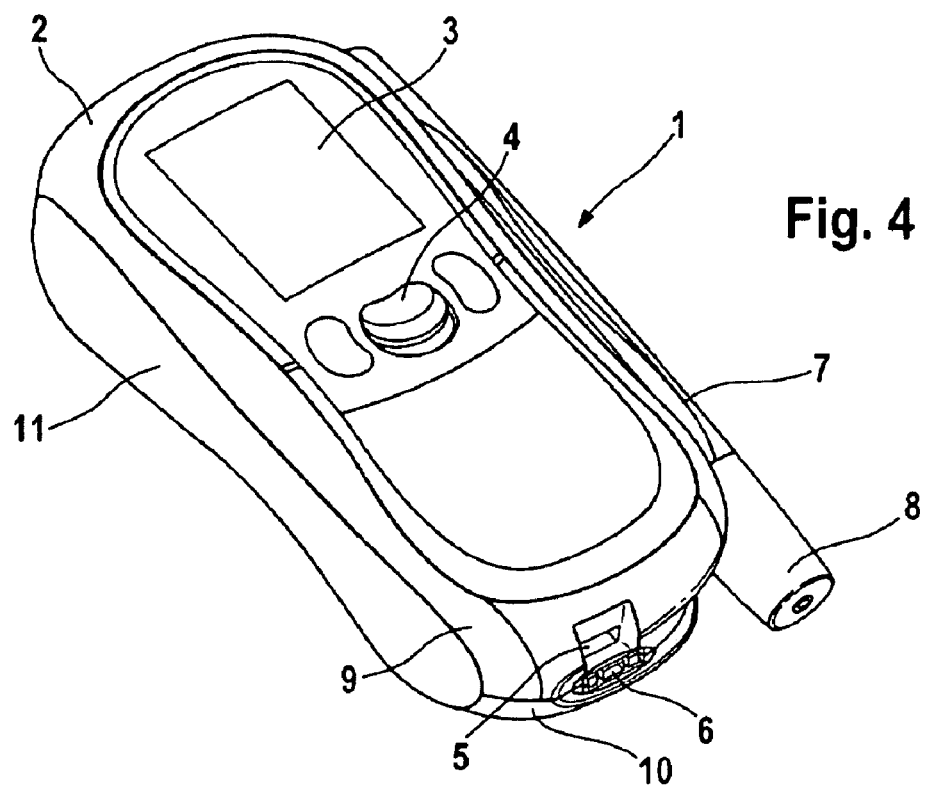
FIG. 4 illustrates a completely assembled analysis device from FIGS. 1 through 3 comprising an embodiment of an engaged lock element according to the present invention.

Referring now to FIG. 4, an embodiment of an assembled analysis device 1 from FIGS. 1 through 3 comprises a lock element 11 fitted in a locked position according to the present invention. As shown, the lock element 11 is configured as an additional housing part, which connects at least two housing parts, such as upper housing part 9 and lower housing part 10 from the illustrated embodiment, and is incorporated into the design of the housing 2 in such a way that its function as a lock is not generally apparent as such to the user of the analysis device 1. In this embodiment, the lock element 11 comprises a component of the overall housing, and may be configured as a housing part or incorporated in a housing part.

In one embodiment, the lock element 11 comprises a load-bearing component of the housing construction, so that it contributes to keeping the housing parts 9, 10 mechanically together. In the exemplary embodiment shown, the lock element 11 comprises a hard plastic part, which is fitted onto one side of the analysis device 1, forming a lateral end of the housing 2 at this point, and may further be configured for more secure grasping of the analysis device 1 by the user through its shaping as a grip part.

In the described embodiments, an analysis device 1 according to the present invention is generally configured for analyzing a medically significant component of a sample, such as a blood glucose measuring device, and comprises a housing 2 having at least two housing parts 9, 10, a measuring unit (not shown) provided in the housing for performing the analysis by a sample, and a processor having software for processing the measured values ascertained by the measuring unit and for preparing analysis measurement data from the measured values. Further according to the embodiments of the present invention, the analysis device 1 comprises a lock element 11, which is configured for locking the housing 2 of the analysis device 1 by producing a generally fixed mechanical connection between the at least two housing parts 9, 10, the analysis device 1 being generally functional for its basic purpose when the lock element 11 is not fitted in a locked position, the housing 2 being locked with the lock element is fitted in the locked position, wherein subsequent reopening of the housing 2 is precluded without the reopening being apparent from structural effects on the housing 2 and/or the lock element 11 caused by the reopening. Typically, such embodiments allow functionality or other quality control checks to be performed on the analysis device during manufacture before the lock element 11 is fitted into the locked position, wherein the analysis device 1 may be tested and if necessary the housing 2 may be opened without destruction for repair of the device 1.

In one embodiment, during use of the analysis device 1, the lock element 11 has no function relating to the operation or operating elements of the analysis device, and/or no function relating to the functioning or complete functioning of the analysis device. In such embodiments, the lock element 11 is generally used for locking the housing 2 of the analysis device 1 by producing a fixed mechanical connection between the at least two housing parts 9, 10. In other embodiments, lock element 11 may be configured to have a functional purpose unrelated to the operation or function of the device 1, such as in regard to the shaping and/or handling of the device 1. The lock element would thus be configured in such a way that it does not exert any function which is required for the complete functioning of the analysis device. Instead, this feature is to be understood to mean that the analysis device is functional or completely functional for its basic purpose (i.e. analyzing a medically significant component of a sample) even without the lock element fitted into a locked position. Such a lock element 11 may provided, e.g., auxiliary functions, for example, in regard to the design, the manual handling (for example, the provision of grip elements for grasping the analysis device), or other auxiliary functions integrated in the lock element or provided for the analysis device by the lock element alone or in interaction with the analysis device.

According to the present invention, using a lock element 11 enables two or more housing parts to be opened again without structural effects (such as destruction) after they are provided in a generally mated orientation but before the lock element is fitted to the housing. Reopening the housing is no longer possible only after fitting the lock element 11 into the locked position. In the solution according to the present invention, an additional housing part is thus employed, which is provided for locking the analysis device. In contrast to sealing, for example, this part may be a component of the overall housing and may be included into the general design of the device 1, so that the "lock" used for locking the housing is not recognizable as such by the user of the analysis device.

In use, because the lock element 11 does not generally exert any function which is required for the basic functioning of the analysis device 1, during assembly the device 1 may be constructed and tested completely even without the lock element 11. If a flaw arises, disassembly and repair may be performed without damage. The lock element 11 is fitted and the device thus locked only after successful testing. In one embodiment, the locking is designed in such a way that damage of the lock element 11 and/or the housing 2 occurs upon opening, thereby ensuring that any opening becomes apparent to the user.

In yet other embodiments of the present invention, a method is provided for producing an to analysis device for analyzing a medically significant component of a sample, such as a blood glucose measuring device, the analysis device comprising a device housing having at least two housing parts, a measuring unit situated in the device housing for performing the analysis by a sample, and a processor having software for processing the measured values ascertained by the measuring unit and for preparing analysis measurement data from the measured values, and the analysis device being subjected to at least one functionality check and closed using a lock element during its production. The method generally comprises the steps of providing such a device with the housing parts in a generally mated but unlocked orientation, performing at least one functionality check on the device, if flaws or other errors are presented then fixing, correcting and/or repairing the device and repeating the at least one functionality check, and if no further flaws or errors are presented then fitting the lock element to the housing so that thereafter reopening of the housing is no longer possible without the reopening being apparent on the housing or the lock element.

In one embodiment, during the assembly of the analysis device, after performing a functionality check of the analysis device, which is completely assembled except for the lock element, the functionality of the basic purpose of the analysis device is tested, and in case of an established functional error, the housing is opened without destruction for correcting the error or repair and the error is corrected, subsequently, to perform a functionality check of the analysis device, the device being completely assembled except for the lock element, the functionality of the analysis device is tested again and then upon the fitting of the lock element on the housing, after performing the further functionality check of the analysis device, the housing is locked.

The features disclosed in the above description, the claims and the drawing may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An analysis device for analyzing a medically significant component of a sample, comprising a housing having an interior and having a measuring unit and a processor each provided in the interior, the measuring unit being configured to perform an analysis on the sample, the processor comprising software configured for processing measured values ascertained by the measuring unit and for preparing data from the measured values, wherein the housing comprises:

at least first, second and third housing parts which integrally define the housing when the housing parts are mated altogether, the first and second housing parts generally defining the interior of the housing when mated together in a generally mated orientation either with or without the third housing part, the first and second housing parts capable of being unmated without damage when mated together without the third housing part, the third housing part comprising a lock element configured for locking the first and second housing parts of the housing in the generally mated orientation by producing a generally fixed mechanical connection between the first and second housing parts which connection is irreversible without damage to at least one of the first, second and third housing parts, the lock element comprising a plurality of catch hooks each configured for insertion into corresponding receptacle openings, each opening being either finitely provided in one or both of the first and second housing parts or cooperatively defined by the first and second housing parts being in the generally mated orientation, wherein the housing has an externally integrated structure when the first, second and third housing parts are mated altogether such that the locking function of the lock element is not generally apparent to a user of the analysis device and each of the first, second and third housing parts define at least a portion of the externally integrated structure;

wherein the analysis device is generally functional for its basic purpose when the first and second housing parts are in a generally mated orientation without the third housing part, such that during manufacture of the analysis device at least one functionality check may be performed on the analysis device being assembled except for the lock element of the third housing part and any of flaws and errors that are presented from said at least one functionality check may be corrected or repaired without damage to any housing parts from unmating the first and second housing parts in order to perform the correction or repair.

2. The analysis device according to claim 1, wherein the locking of the housing by the lock element is configured to cause damage to the lock element upon the reopening of the housing.

3. The analysis device according to claim 1, wherein the lock element engages housing parts in such a way that removing the lock element is precluded without causing destruction of the lock element.

4. The analysis device according to claim 1, wherein the lock element comprises a predetermined breaking point configured to break upon at least one of reopening of the housing and removal of the lock element, when the lock element is in the locked position.

5. The analysis device according to claim 1, wherein the lock element comprises a load-bearing component of the housing construction and is configured to contribute to keeping the housing parts mechanically together.

6. The analysis device according to claim 1, the analysis device comprising a device selected from the group consisting of a blood glucose meter, a cholesterol measuring device, and a blood coagulation parameter measuring device, wherein the sample comprises a bodily fluid.

7. The analysis device according to claim 1, wherein the device comprises a portable analysis device which may be manually handled, manually actuated, and manually operated by a user.

* * * * *